United States Patent
Shiels

(10) Patent No.: US 10,456,142 B2
(45) Date of Patent: Oct. 29, 2019

(54) SURGICAL SAW AND SAW BLADE FOR USE THEREWITH

(71) Applicant: MAKO Surgical Corp., Ft. Lauderdale, FL (US)

(72) Inventor: Paul Shiels, Albuquerque, NM (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 195 days.

(21) Appl. No.: 15/612,119

(22) Filed: Jun. 2, 2017

(65) Prior Publication Data

US 2017/0348007 A1    Dec. 7, 2017

Related U.S. Application Data

(60) Provisional application No. 62/345,306, filed on Jun. 3, 2016.

(51) Int. Cl.
*A61B 17/00* (2006.01)
*A61B 17/14* (2006.01)

(52) U.S. Cl.
CPC .. *A61B 17/142* (2016.11); *A61B 2017/00477* (2013.01)

(58) Field of Classification Search
CPC combination set(s) only.
See application file for complete search history.

(56) References Cited

U.S. PATENT DOCUMENTS

| | | | |
|---|---|---|---|
| 3,384,085 A | 5/1968 | Hall | |
| RE27,032 E | 1/1971 | Hall | |
| 3,964,163 A | 6/1976 | Russo | |
| 4,157,231 A | 6/1979 | Phillips | |
| 4,513,742 A * | 4/1985 | Arnegger | B23D 61/006 30/350 |
| 4,637,391 A | 1/1987 | Schlein | |
| 4,657,428 A * | 4/1987 | Wiley | B24B 45/006 403/359.3 |
| 4,985,031 A | 1/1991 | Buss et al. | |
| 5,147,364 A | 9/1992 | Comparetto | |
| 5,178,626 A | 1/1993 | Pappas | |
| 5,382,249 A * | 1/1995 | Fletcher | B23D 51/10 606/176 |

(Continued)

FOREIGN PATENT DOCUMENTS

| | | |
|---|---|---|
| CN | 204218977 U | 3/2015 |
| JP | 2002 349959 A | 12/2002 |

OTHER PUBLICATIONS

Stryker Instruments, "Cutting Accessories", published at least as early as Jun. 3, 2016; pp. 5-7.

(Continued)

*Primary Examiner* — Christian A Sevilla
(74) *Attorney, Agent, or Firm* — Howard & Howard Attorneys PLLC

(57) ABSTRACT

A surgical saw blade for being coupled to a drive hub of a surgical saw. The surgical saw blade includes an attachment portion configured to be removably coupled to the drive hub. The surgical saw blade also includes a cutting portion opposite the attachment portion that includes a plurality of teeth. Additionally, the attachment portion defines a pair of indents. The first indent and the second indent are each defined by at least one curved surface. The curved surface is radially outwardly convex.

17 Claims, 13 Drawing Sheets

(56) References Cited

U.S. PATENT DOCUMENTS

| | | | |
|---|---|---|---|
| 5,395,377 | A | 3/1995 | Petersen et al. |
| 5,423,845 | A * | 6/1995 | McDaniel ............ B23D 61/121 |
| | | | 30/355 |
| 5,496,316 | A | 3/1996 | Goris |
| 5,496,325 | A | 3/1996 | McClees |
| 5,533,842 | A | 7/1996 | Johnson et al. |
| 5,578,039 | A | 11/1996 | Venderely et al. |
| 5,653,714 | A | 8/1997 | Dietz et al. |
| 5,779,702 | A | 7/1998 | Fard |
| 6,022,353 | A | 2/2000 | Fletcher et al. |
| 6,342,057 | B1 | 1/2002 | Brace et al. |
| 7,691,106 | B2 | 4/2010 | Schenberger et al. |
| 7,901,424 | B2 | 3/2011 | Fletcher et al. |
| 8,052,692 | B2 | 11/2011 | Lionberger et al. |
| 8,100,912 | B2 | 1/2012 | Marietta |
| 8,246,620 | B2 | 8/2012 | Holko et al. |
| 8,323,285 | B2 | 12/2012 | Walen et al. |
| 8,491,596 | B2 | 7/2013 | Long et al. |
| 8,672,943 | B2 | 3/2014 | Fisher et al. |
| 8,734,450 | B2 | 5/2014 | Landon |
| 8,814,872 | B2 | 8/2014 | Bickenbach |
| 8,888,783 | B2 | 11/2014 | Young |
| 8,920,424 | B2 * | 12/2014 | Boykin .................... A61C 3/12 |
| | | | 606/82 |
| 8,939,981 | B1 | 1/2015 | Nelson |
| 9,033,986 | B2 | 5/2015 | Nelson et al. |
| 9,119,631 | B1 | 9/2015 | Murphy |
| 9,414,845 | B2 | 8/2016 | Boykin |
| 9,468,445 | B2 | 10/2016 | McGinley et al. |
| 9,498,231 | B2 | 11/2016 | Haider et al. |
| 2003/0236522 | A1 | 12/2003 | Long et al. |
| 2004/0073235 | A1 * | 4/2004 | Lund .................. A61B 17/1227 |
| | | | 606/151 |
| 2004/0204731 | A1 | 10/2004 | Gant |
| 2008/0027442 | A1 | 1/2008 | Blue |
| 2009/0138017 | A1 | 5/2009 | Carusillo et al. |
| 2012/0089012 | A1 | 4/2012 | Baur et al. |
| 2012/0130380 | A1 | 5/2012 | Babaev |
| 2012/0289963 | A1 * | 11/2012 | LeGrand .................. B27B 5/32 |
| | | | 606/79 |

OTHER PUBLICATIONS

English language abstract and machine-assisted English language translation of Japanese Publication No. JP 2002 349959 A extracted from www.espacenet.com on Aug. 10, 2017; 10 pages.

English language abstract and machine-assisted English language translation of Chinese Publication No. CN204218977 U extracted from www.espacenet.com on Aug. 10, 2017; 5 pages.

* cited by examiner

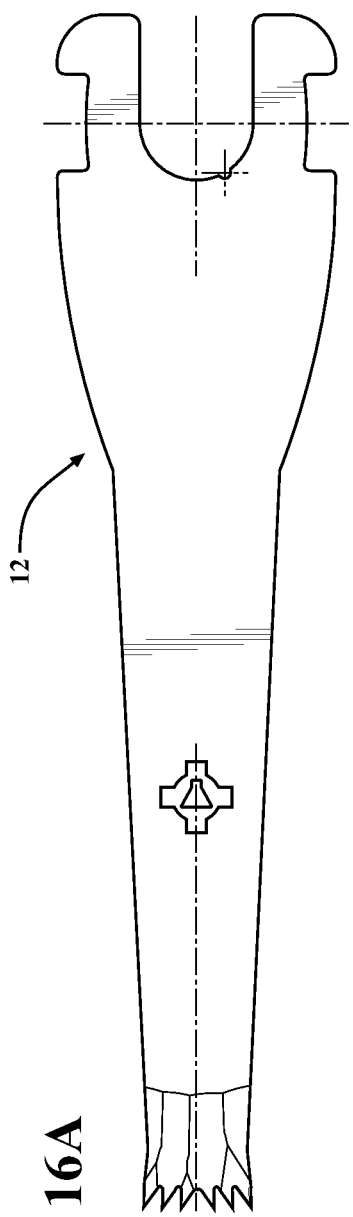
FIG. 16A
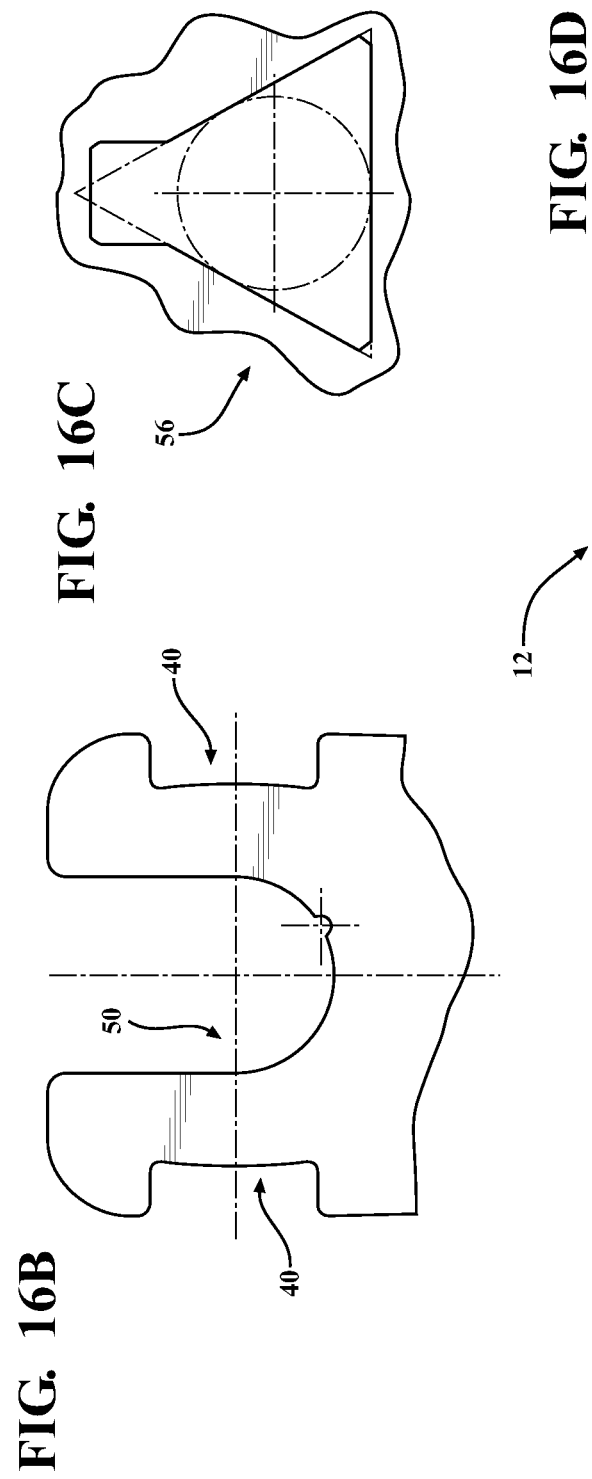
FIG. 16B
FIG. 16C
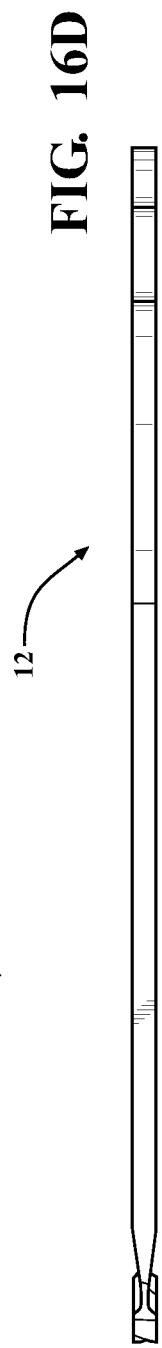
FIG. 16D

SURGICAL SAW AND SAW BLADE FOR USE THEREWITH

RELATED APPLICATIONS

This application claims priority to and the benefit of U.S. Provisional Patent Application No. 62/345,306, filed on Jun. 3, 2016, the entire contents of which are hereby incorporated by reference.

TECHNICAL FIELD

The embodiments described herein generally relate to surgical saws and saw blades for use therewith.

BACKGROUND

It is prevalent to use powered surgical saws during surgical procedures. Generally, these surgical saws have a handpiece which may include an electric or pneumatic motor disposed within the handpiece. A driver is operatively coupled to the motor to be driven in an oscillating manner by the motor. An attachment portion of a surgical saw blade is releasably coupled to the driver. At the opposite end of the blade is a cutting portion which includes teeth. The blade may be provided in various configurations, including straight or crescentic. The blades may be disposable.

Generally, the driver comprises one or more drive bosses to which the attachment portion of the blade is coupled. When the motor drives the driver, force is applied by the drive bosses to the attachment portion of the blade, which consequently applies a cutting force to the cutting portion of the blade to cut through material. Forces acting on the drive bosses and the attachment portion during cutting may compromise the drive bosses or the attachment portion of the blade itself. This may result in premature wear on the drive bosses and/or the attachment portion of the blade and/or unintentional release or slippage of the blade relative to the drive bosses. In many cases, the driver and associated drive bosses are designed to be reusable such that any premature wear is undesirable.

A surgical saw and blades for use therewith designed to be simple and effective while overcoming one or more of the aforementioned challenges is desired.

BRIEF DESCRIPTION OF THE DRAWINGS

FIG. 16A is a top plan view of one embodiment of the blade.

FIG. 16B is a top plan view of a portion of the blade shown in FIG. 16A.

FIG. 16C is a top plan view of another portion of the blade shown in FIG. 16A.

FIG. 16D is a side view of the blade shown in FIG. 16A.

DETAILED DESCRIPTION

Figure 1:
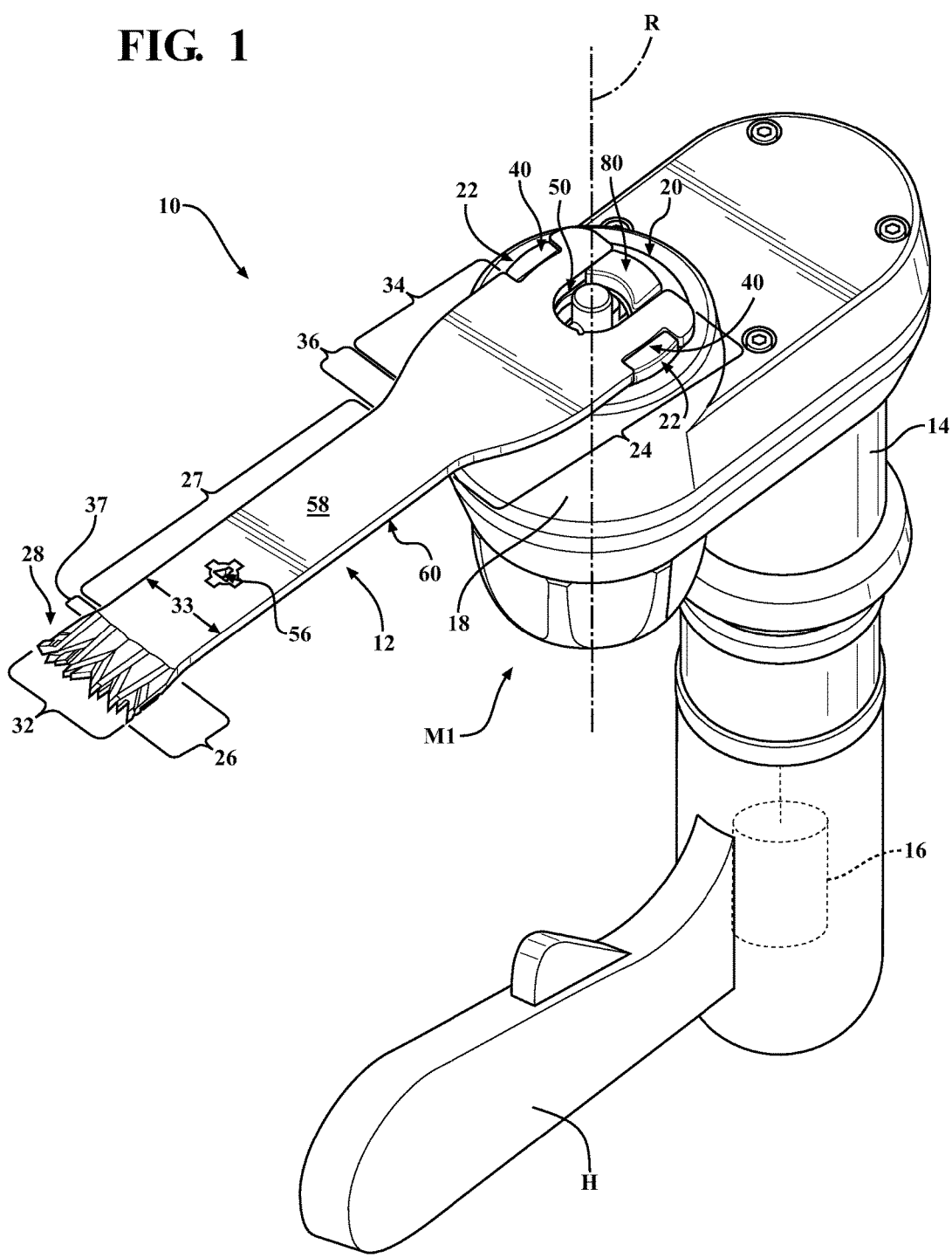
FIG. 1 is a perspective view of a surgical saw assembly with a right angle coupler for attaching to a handpiece, such as an end effector of robotic arm.
Figure 2:
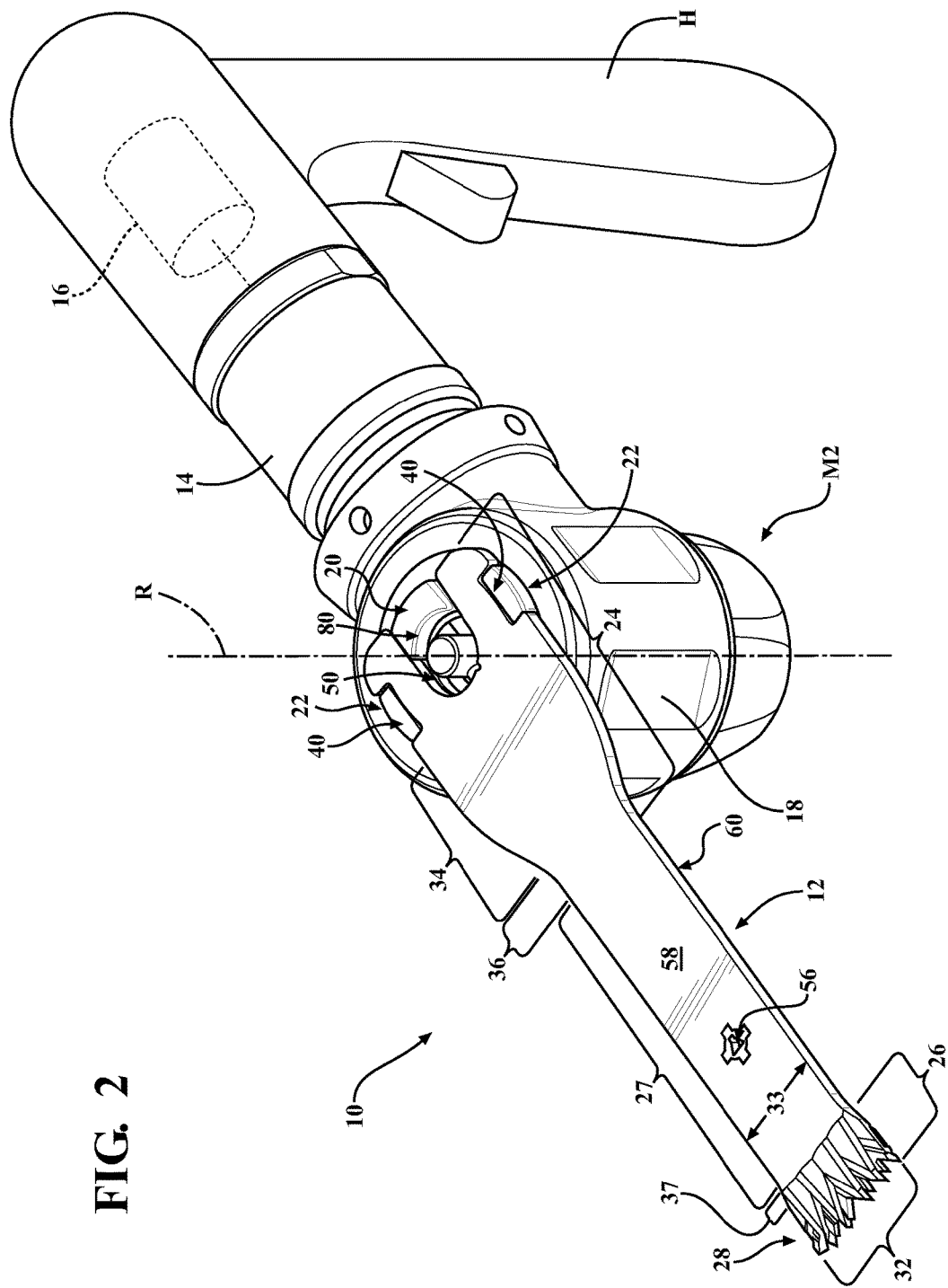
FIG. 2 is a perspective view of the surgical saw assembly with a straight coupler for attaching to the handpiece.

Referring to FIGS. 1 and 2, a surgical saw assembly 10 is shown for use during surgical procedures. The surgical procedures may be orthopedic surgeries, brain surgeries, cardiovascular surgeries or any other surgeries requiring the use of a cutting instrument. The surgical saw assembly 10 includes a surgical saw blade 12. The blade 12 may be of various shapes and sizes such as a crescentic blade or a straight blade. The surgical saw assembly 10 shown in FIG. 1 has a right angle coupler M1 for attaching to a handpiece H, such as an end effector of a surgical robotic arm (not shown), and the surgical saw assembly in FIG. 2 has a straight coupler M2 for attaching to the handpiece H.

The couplers M1, M2 comprise a coupler housing 14 for attaching to the handpiece H. A motor 16 may be located in the handpiece H (as shown) or in the housing 14 attached to the handpiece H. The motor 16 may be of any suitable type, including but not limited to a pneumatic or electrical motor. The motor 16 is configured to provide oscillating motion to the blade 12. It is contemplated that the motor 16 may provide cyclical linear motion and/or cyclical angular motion, such as used for an oscillating sagittal saw.

Figure 17:
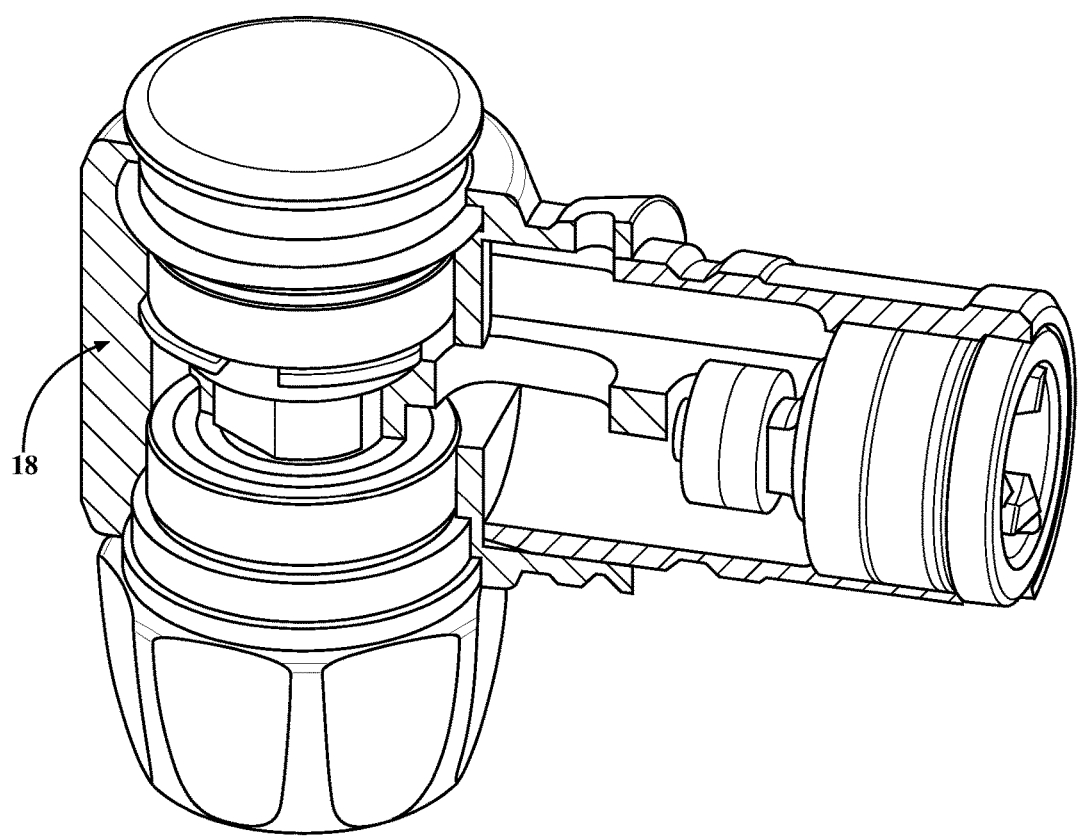
FIG. 17 is a partial cut away perspective view of the surgical saw assembly without the blade.

The motor 16 is operatively coupled to a driver 18. The driver 18 transfers drive torque from the motor 16 to the blade 12. The driver 18 is at least partially disposed within the housing 14 and includes a drive hub 20. The drive hub 20 is configured to releasably receive the blade 12. As illustrated in FIGS. 1 and 2, the drive hub 20 may include one or more primary drive bosses 22 adapted to engage the blade 12. The driver 18, including the drive hub 20, may oscillate due to torque from the motor 16 which in turn will oscillate the blade 12 about a rotation axis R. In addition to the drive hub 20, the driver 18 comprises additional components to convert torque from a drive shaft of the motor 16 into oscillating motion of the drive hub 20. Examples of such components are shown in FIG. 17 and in U.S. Pat. No.

8,100,912 to Marietta, hereby incorporated by reference. In other embodiments, the drive shaft of the motor 16 may directly drive the drive hub 20 to rotate the drive hub 20 and may oscillate the drive hub 20, or rotate the drive hub 20 in complete rotations in one direction and/or another.

Figure 3:
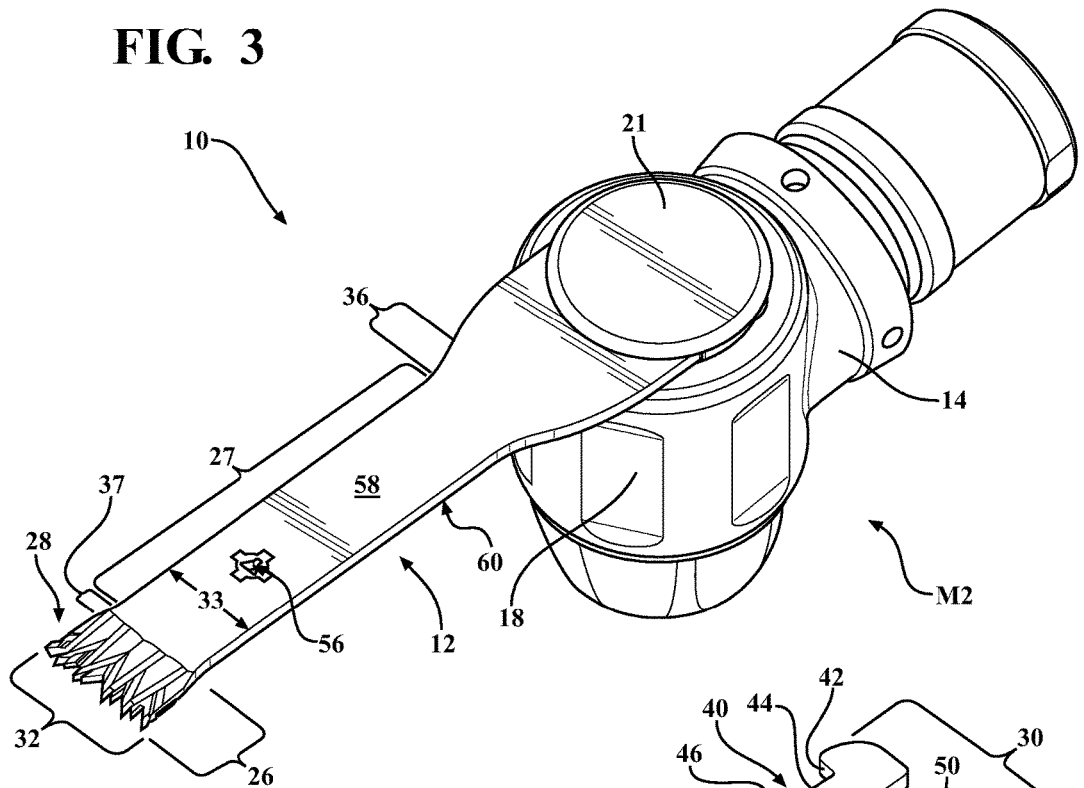
FIG. 3 is a perspective view of the surgical saw assembly of FIG. 2 having a cap.

As illustrated in FIG. 3, the blade 12 may be secured to the drive hub 20 using a cap 21. The cap 21 is adapted to be coupled to the drive hub 20 with the blade 12 disposed between the drive hub 20 and the cap 21. The cap 21 may be round as illustrated in the embodiment shown in FIG. 3, or may be any other shape including oval or rectangular. It is contemplated that the cap 21 is configured to help secure the blade 12 onto the drive hub 20. The cap 21 may be friction fitted onto the drive hub 20 or other portion of the driver 18 or may be secured by other mechanisms. The cap 21 has been removed in FIGS. 1 and 2 for illustration.

Referring to FIGS. 1 and 2, the blade 12 includes an attachment portion 24 configured to be removably coupled to the drive hub 20. Opposite the attachment portion 24, the blade 12 includes a cutting portion 26 which has a plurality of teeth 28. A body portion 27 extends between the attachment portion 24 and the cutting portion 26. The attachment portion 24 of the blade 12, in the embodiment shown, generally has a width 30 (see FIG. 5) greater than a width 32 of the cutting portion 26. In some embodiments, the blade 12 is formed from a single piece of material, such as metal, by stamping and/or machining.

Figure 4:
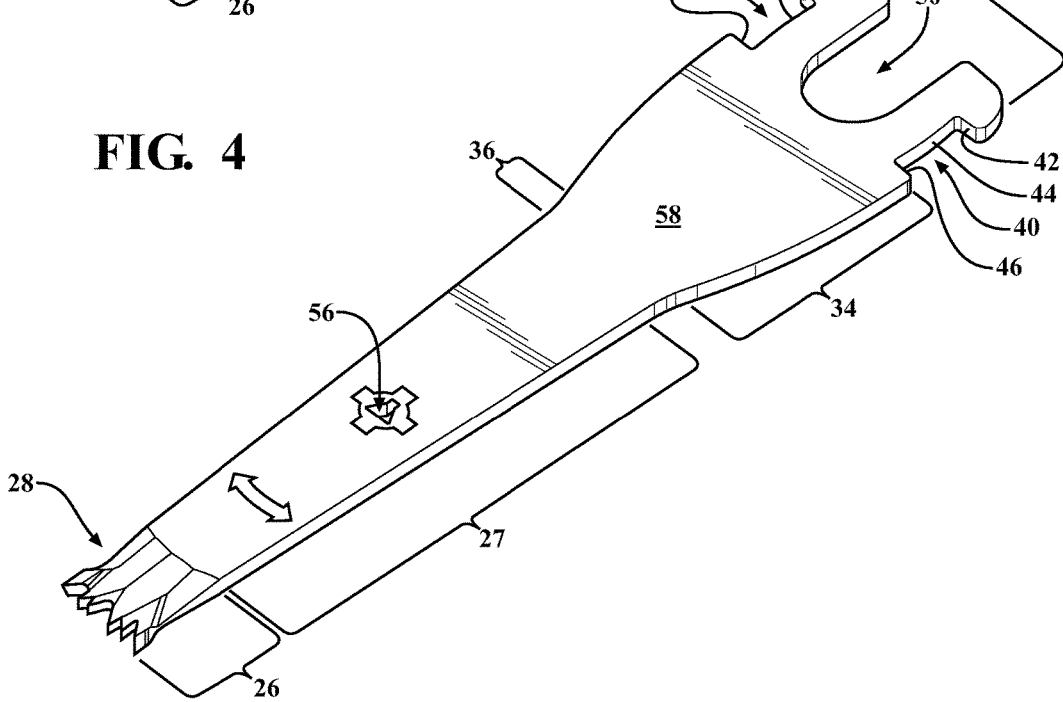
FIG. 4 is a perspective view of a surgical saw blade.

The attachment portion 24 includes a tapered section 34 which gradually gets narrower until it reaches a transition section 36. Opposite the transition section 36 from the attachment portion 24 is the body portion 27. The body portion 27 may have a continuous width 33 from the transition section 36 to the cutting portion 26, or as illustrated in FIG. 4, the body portion 27 may gradually get narrower in width as the body portion 27 approaches the cutting portion 26. In other embodiments, the body portion 27 may gradually get wider in width as the body portion 27 approaches the cutting portion 26. Outer side surfaces of the blade 12 at the attachment portion 24 and the body portion 27 may be perpendicular to top and bottom surfaces 58, 60 of the blade 12.

It is contemplated that the length of the attachment portion 24 is less than the length of the body portion 27, however, many other configurations have been contemplated. Moreover, the length of the cutting portion 26 may be less than the length of the attachment portion 24 and less than the length of the body portion 27. As illustrated, the body portion 27 is generally elongate and rectangularly shaped while at least a portion of the attachment portion 24 may include curves. It is also contemplated that the attachment portion 24 and/or the body portion 27 may be of various other configurations.

Moreover, as best shown in FIGS. 1-3, the body portion 27 may reach a second transition section 37 which is disposed between the body portion 27 and the cutting portion 26. The second transition section 37 may have a different, typically smaller, width than the width of the teeth 28 and the width of the body portion 27. It is also contemplated that the second transition section 37 may taper inwards from the body portion 27 before once again tapering outwards towards the teeth 28 of the cutting portion 26.

Figure 5:
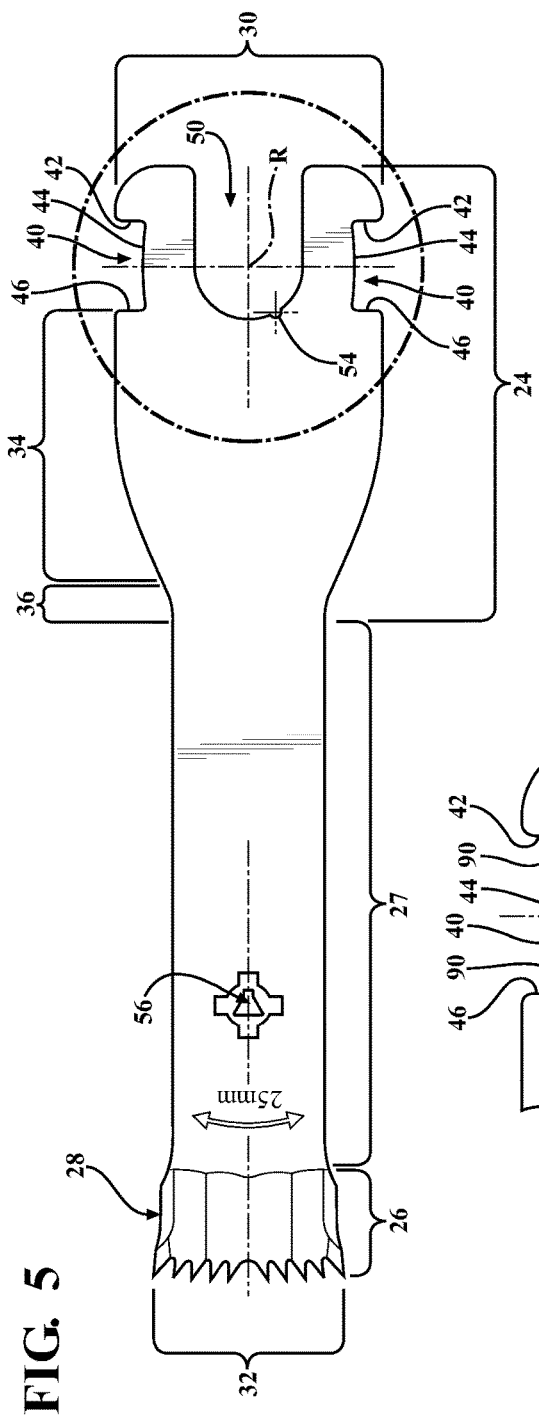
FIG. 5 is top plan view of the blade.
Figure 6:
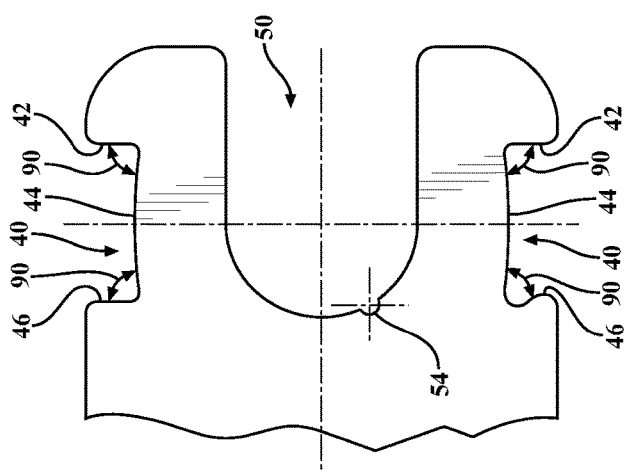
FIG. 6 is a top plan view of a portion of the blade.

As best illustrated in FIGS. 4-6, the blade 12 defines primary indents 40 on the attachment portion 24. The primary indents 40 are disposed on opposite lateral sides of the attachment portion 24 and are disposed completely through the thickness of the blade 12. Each of the primary indents 40 are defined by a first side 42, a second side 44, and a third side 46 with the first 42 and third side 46 being generally perpendicular to the second side 44. Moreover, the second side 44 is disposed between the first side 42 and the third side 46. In the embodiment shown, the second side 44 is integral and smoothly continuous with the first side 42 and the third side 46 by virtue of rounded profile transitions therebetween, described further below. An indent space is formed by the first side 42, the second side 44, and the third side 46.

At least one of the first side 42, the second side 44, and the third side 46 is curved, or non-linear in profile (as viewed in a top view). In the Figures, the second side 44 is shown as the curved portion, however, it is contemplated that the first side 42 and/or the third side 46 may additionally, or alternatively be curved in profile. The curved portion is shown as a surface that is generally convex in shape in profile and protrudes convexly outwardly from the rotation axis R into the indent space. In other words, the indent space is narrower in the middle of the second side 44 than at the ends of the second side 44 when the second side 44 is curved. As shown in FIG. 5, a center of each of the primary indents 40 lies along a lateral line that passes through the rotational axis R of the blade 12.

Additionally, the blade 12 includes a central indent 50. The central indent 50 is generally 'U' shaped and has a free space disposed between the primary indents 40 about the rotational axis R. The central indent 50 may also include a notch 54. The notch 54 may be configured to engage a portion of the drive hub 20, such as a smaller boss (not shown) protruding upwardly into the notch 54. As illustrated in the Figures, the notch 54 is disposed off to one side of center of the central indent 50 so that the blade 12 is properly fitted with the top surface 58 facing upwardly. Other configurations are contemplated. It is also contemplated that the notch 54 may be disposed along any portion of the central indent 50.

Figure 16E:
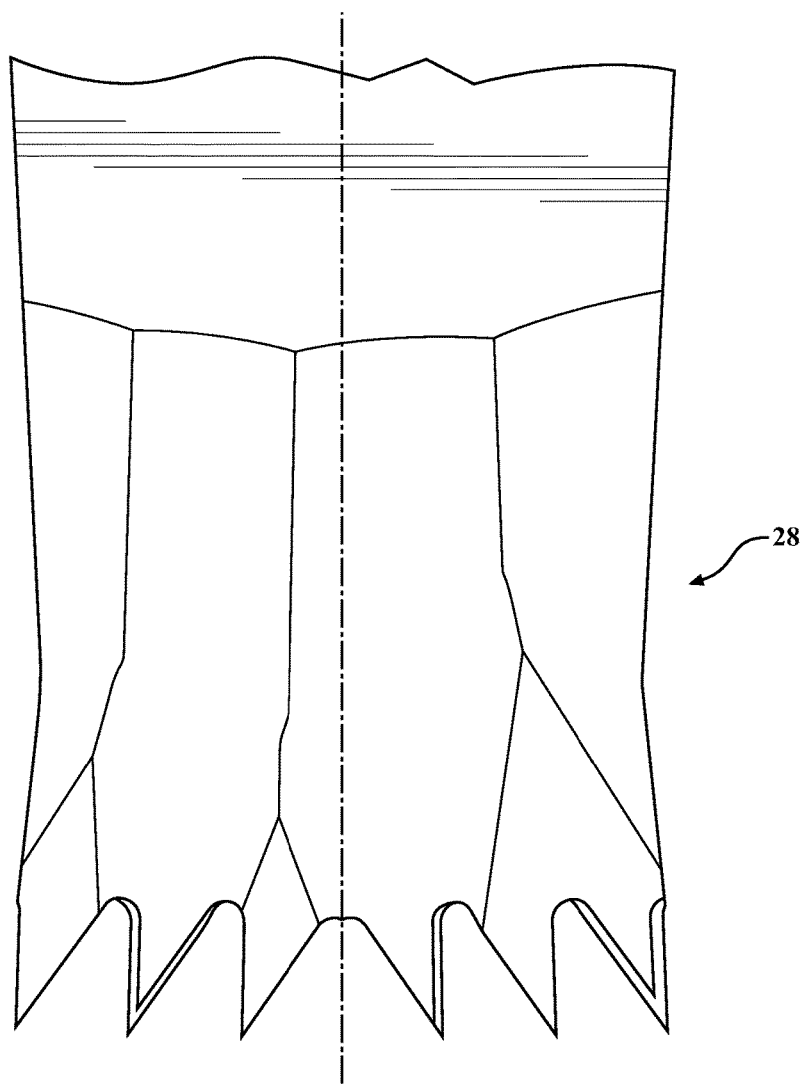
FIG. 16E is a top plan view of the cutting portion of the blade shown in FIG. 16A.

The blade 12 may include an aperture 56 disposed on the body 27. As illustrated in FIGS. 4 and 5, the aperture 56 is generally triangularly shaped and is disposed completely through the entire thickness of the blade 12. It is also contemplated that the aperture 56 may also be cylindrical, a drill hole, or any other shape. The aperture 56 may be used to allow checking of the registration of the blade 12 by a navigation pointer of a surgical navigation system from either a top surface 58 or a bottom surface 60 of the blade 12. An example of a possible configuration of the aperture 56 is shown in FIG. 16C.

The blade 12 may also include text or other indicia on the top surface 58 of the blade 12. The indicia may include an arrow (see FIG. 4) indicating the swing arc of the blade 12, i.e., the distance each tip of each tooth on the blade 12 travels during oscillation or other swing movements, or distances of travel off on any other point on the blade 12. Moreover, the text may include the width 32 of the blade 12 at the cutting portion 26 or at the teeth 28. Additionally, the text may include indication of the manufacturer or other identifying information.

Figure 10A:
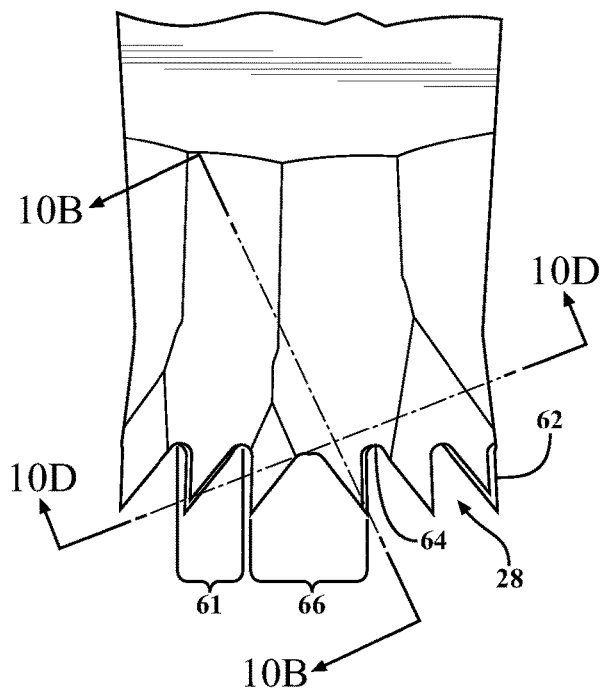
FIG. 10A is a top plan view of the cutting portion of the blade.
Figure 10B:
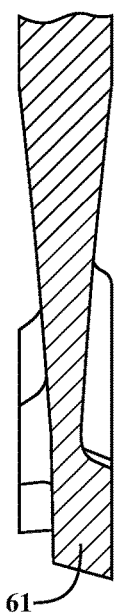
FIG. 10B is a cross-sectional view along line 10B-10B of the blade shown in FIG. 10A.
Figure 10C:
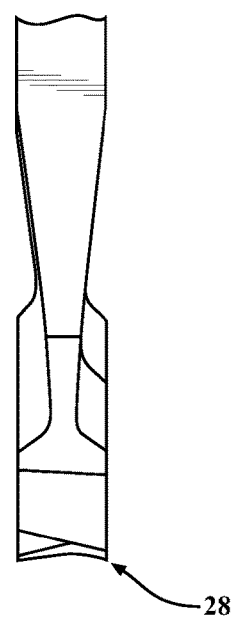
FIG. 10C is a side view of the cutting portion of the blade shown in FIG. 10A.
Figure 10D:
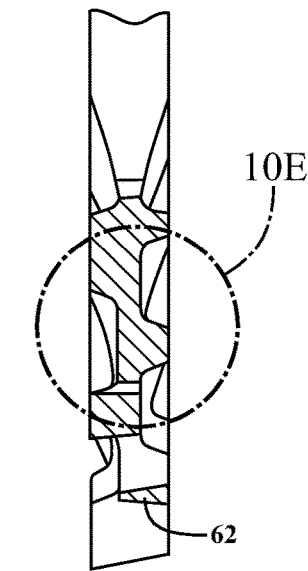
FIG. 10D is a cross-sectional view along line 10D-10D of the blade shown in FIG. 10A.
Figure 10E:
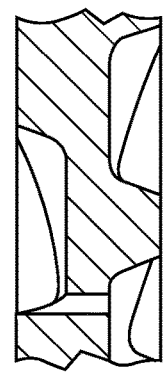
FIG. 10E is a close up detail of the cross section shown in FIG. 10D.

The blade 12 may have a thickness greater than conventional sagittal saw blades. The greater thickness makes the blade 12 stiffer than thinner blades and limits flexing (e.g. as a result of skiving) of the blade 12 while cutting during a surgical procedure. In one embodiment, the blade 12 is designed to limit flexing to 0.2 mm or less upon application of a 2.2 N load. In the embodiment shown, the thickness is approximately 2 mm which provides the teeth 28 with three dimensional geometry that improves strength and cutting ability of the blade 12. The thickness of the blade 12 may be from 1 mm to 3 mm, from 1.5 mm to 2.5 mm, from 1.9 mm to 2.2 mm, or other thicknesses. It is contemplated that the blade 12 may have a uniform thickness throughout the entire length of the blade 12. It is also contemplated that at least a portion of the blade 12 may have a different thickness from the remainder of the blade 12. For example, it is contemplated that the blade 12 may have a uniform thickness along the attachment portion 24 and body portion 27 and may transition to a different thickness at the cutting portion 26, including the teeth 28. Additionally, each of the attachment portion 24, the body portion 27, and the cutting portion 26 may have different thicknesses. In the embodiment illustrated in FIGS. 10A-E, and best illustrated in FIG. 10C, the thickness of the blade 12 gets thinner at the beginning of the cutting portion 26 before jutting out to the same thickness towards the end of the teeth 28.

As best illustrated in FIGS. 7-10E, the teeth 28 have generally triangularly shaped profiles and may vary in size. Moreover, the teeth 28 may vary in thickness from the remainder of the blade 12 or from each other. Additionally, it is contemplated that a single tooth 61 may have a varied thickness and may taper in thickness from its base to its tip. Each tooth may have an angled cutting edge 62 so that a width of the tooth 61 in profile when viewed from a top view is less than a width of the same tooth 61 in profile when viewed from a bottom view.

The angled cutting edge 62 of each tooth 61 may be configured to provide a cutting advantage in one direction of motion, while an angled cutting edge of an adjacent tooth 61 provides a cutting advantage in an opposite direction. For instance, in the embodiment of FIG. 8A, three of the teeth 28 may cut best in one direction, while the others cut best in the opposite direction. Additionally, some adjacent teeth may be at least partially offset in a direction of the thickness of the blade 12 so that the tips of the teeth 28 are staggered to provide a kerf in the material being cut that is at least as thick as a thickest part of the cutting portion 26. In the embodiment shown in FIGS. 10A-10E, the two outermost of the teeth 28 have a tip of a first thickness (such as around 2 mm), while inner teeth (between the two outermost teeth) have tips of a second thickness less than the first thickness and the inner teeth are staggered to provide cutting at different levels in the material being cut.

Figure 7:
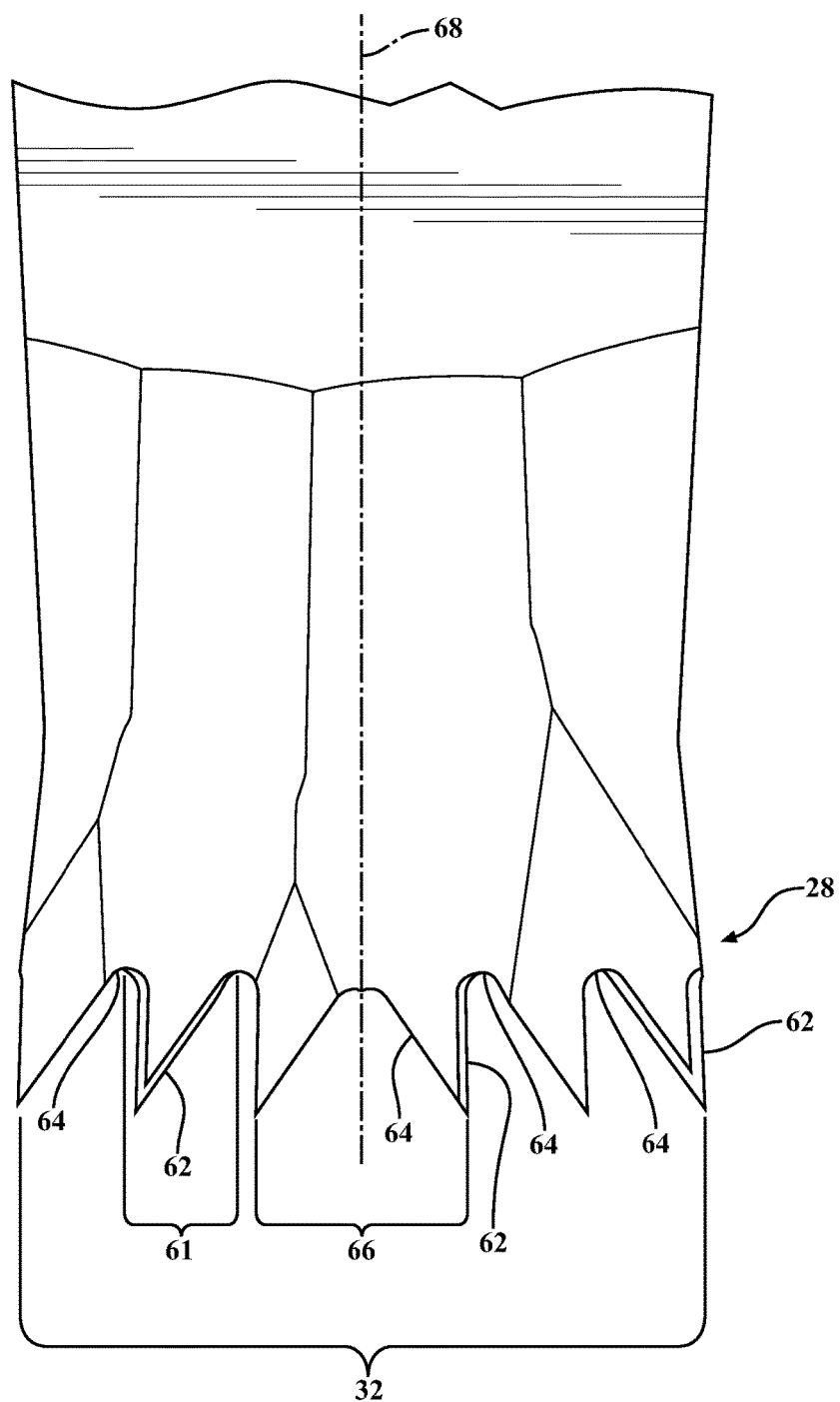
FIG. 7 is a top plan view of a cutting portion of the blade.
Figure 8A:
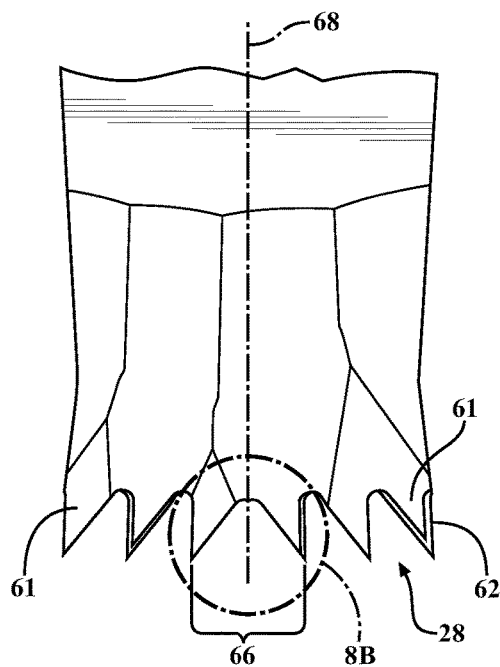
FIG. 8A is a top plan view of the cutting portion of the blade.
Figure 8B:
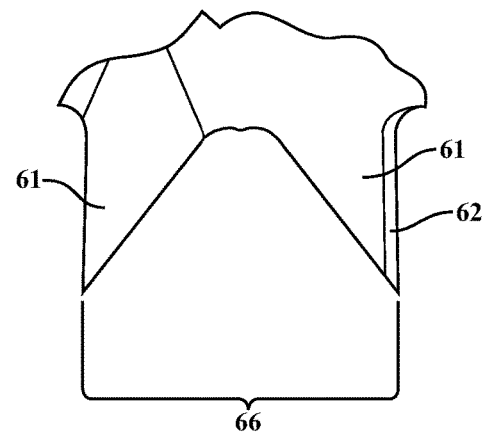
FIG. 8B is a close up detail of adjacent teeth of the cutting portion shown in FIG. 8A.
Figure 9A:
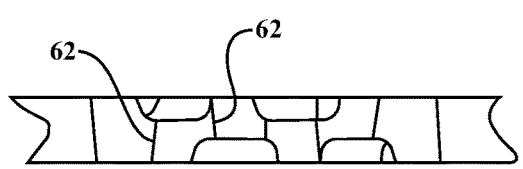
FIG. 9A is an end view of the cutting portion of the blade.
Figure 9B:
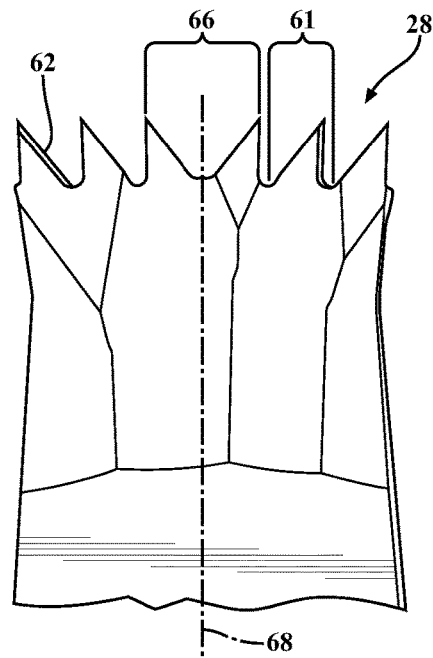
FIG. 9B is another view of the cutting portion of the blade shown in FIG. 9A.

As additionally shown in FIG. 7, the cutting portion 26 may have a rounded section 64 or gullet disposed between adjacent teeth 28. It is also contemplated that the rounded section 64 may be of any of shape or configuration. The rounded sections 64 may have various radii such that a distance between individual teeth 28 may vary. In the embodiment shown in FIG. 7, a middle portion 66 has a wider rounded portion 64 such that the teeth 28 on either side of center line 68 are further apart than the remainder of the teeth 28. As additionally illustrated in FIGS. 7-10E, each of the individual teeth 28 are generally right angled triangles with hypotenuses facing opposite directions on opposite sides of the center line 68. However, various configurations have been contemplated.

Figure 11:
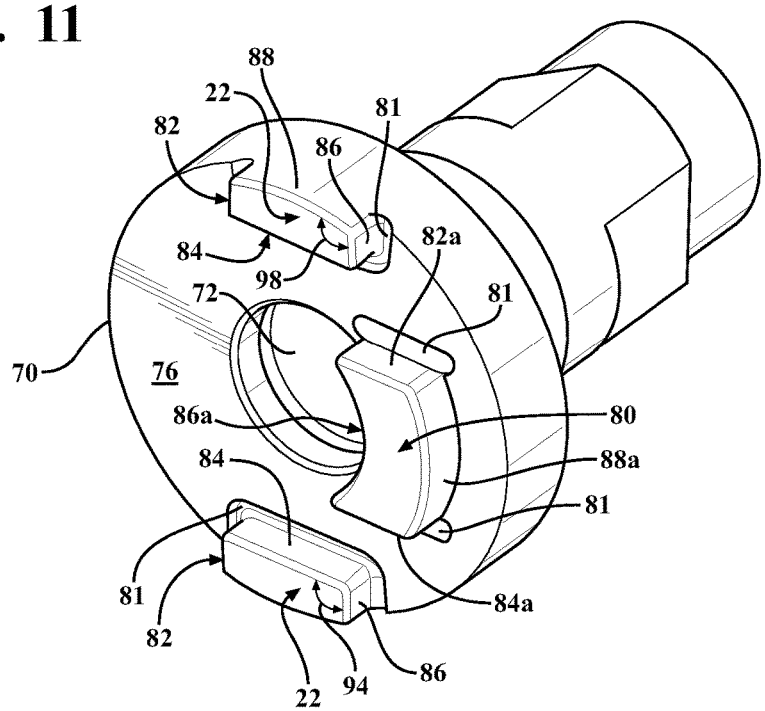
FIG. 11 is a perspective view of a driver shown removed from the surgical saw assembly.

Referring now to FIG. 11, the drive hub 20 has a generally circular outer periphery 70 and includes the primary drive bosses 22. The drive hub 20 also includes a generally circular opening 72 disposed in the center of the drive hub 20. In the illustrated embodiment, the drive hub 20 includes two primary drive bosses 22 disposed opposite to one another, but identical in configuration. Each of the primary drive bosses 22 protrude radially inwardly from the outer periphery 70 of the drive hub 20. Additionally, the drive hub 20 includes a central drive boss 80 disposed partially about the circular opening 72. Aside from the drive bosses 22, 80, the drive hub 20 has a generally flat support surface 76 adjacent to the drive bosses 22, 80 on which the flat bottom surface 60 of the blade 12 is supported.

In the embodiment illustrated in FIG. 11, the primary drive bosses 22 have a first surface 82, a second surface 84, and a third surface 86 which are generally flat, with the first 82 and third surfaces 86 disposed parallel to one another. The primary drive bosses 22 also have an outer fourth surface 88 that is continuous with the outer periphery 70. On the central drive boss 80, opposite first and second surfaces 82a, 84a are flat in shape while a third surface 86a, disposed about the circular opening 72, is arcuate and identical in shape to a fourth surface 88a. It is contemplated that various other shapes and sizes of drive bosses 22 are possible.

Figure 12:
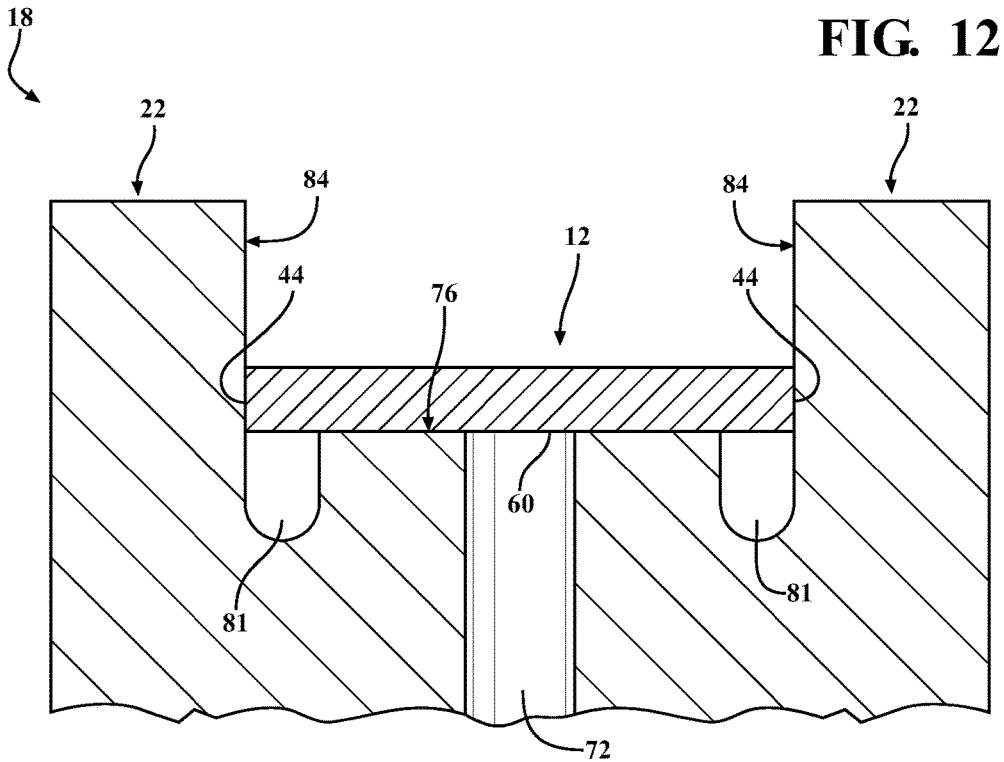
FIG. 12 is a cross-sectional view of a portion of the driver having the blade attached to the driver.

Referring still to FIG. 11, the drive hub 20 also includes a plurality of recesses 81 or grooves defined in the support surface 76. The recesses 81 are disposed adjacent to each of the drive bosses 22, 80. It is contemplated that the recesses 81 may be disposed adjacent to one or more of the surfaces 82, 84, 86, 88, 82a, 84a, 86a, 88a of each of the drive bosses 22, 80. As illustrated in FIG. 11, the recesses 81 may extend at least the entire length of one or more of the surfaces 82, 84, 86, 88, 82a, 84a, 86a, 88a. As illustrated in FIG. 12, the recesses 81 allow the bottom surface 60 of the blade 12 to lie flat on the support surface 76 of the drive hub 20 while the sides 42, 44, 46 of the blade 12 contact the one or more surfaces 82, 84, 86, 88, 82a, 84a, 86a, 88a of the drive bosses 22, 80, as shown in FIG. 12. This configuration reduces wear on the drive bosses 22, 80 during operation of the surgical saw 10 by providing a flat surface of the drive bosses 22, 80 against which a corresponding side 42, 44, 46 of the blade 12 can sufficiently contact (such as the curved side surface 44 described herein—albeit in that case only one line of contact is made).

In the embodiment shown, the surfaces 82, 84, 86, 88, 82a, 84a, 86a, 88a of the drive bosses 22, 80 are generally perpendicular to the top 58 and bottom 60 surfaces of the blade 12 when the blade 12 is coupled to the drive hub 20. The sides 42, 44, 46 of the blades 12 may also be perpendicular to the top 58 and bottom 60 surfaces of the blade 12. Without the recesses 81, during normal machining, rounded transitions may be created between one or more of the side surfaces 82, 84, 86, 88, 82a, 84a, 86a, 88a of the drive bosses 22, 80 and the support surface 76, which may prevent sufficient seating of the sides 42, 44, 46 of the blade 12 against the drive bosses 22, 80 and cause undesirable wear of the drive bosses 22, 80. The recesses 81 enable machining to occur below the support surface 76 thereby creating such rounded transitions below the support surface 76 and out of the way of the bottom surface 60 of the blade 12.

Figure 13:
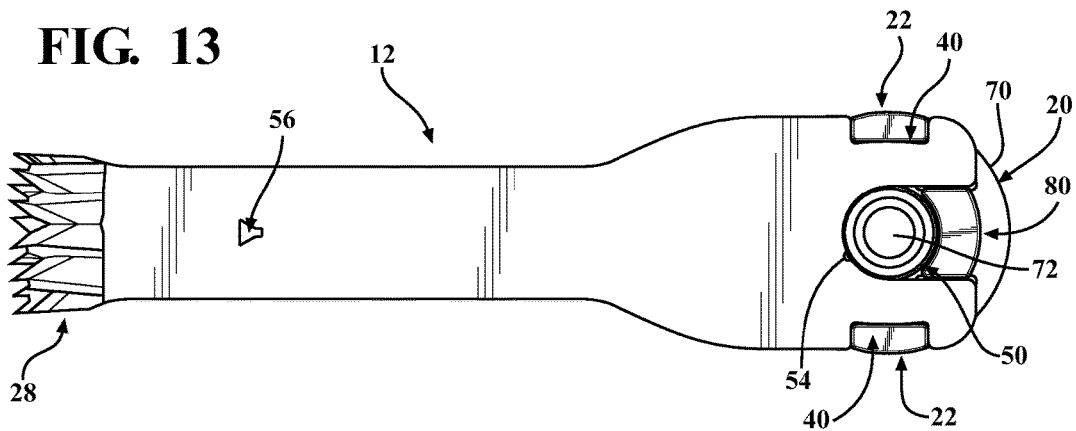
FIG. 13 is a top plan view of the blade attached to the driver.
Figure 14:
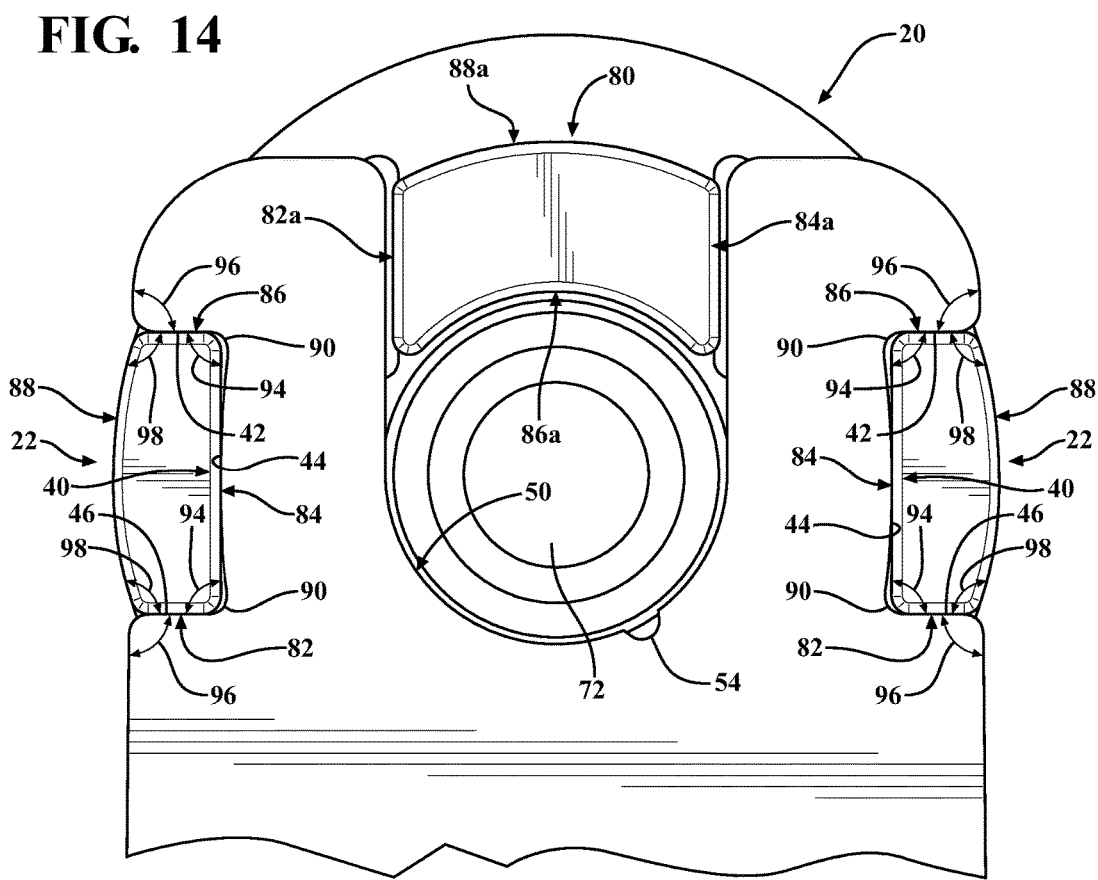
FIG. 14 is a top plan view of a portion of the blade attached to the driver.

Referring now to FIGS. 13 and 14, the drive bosses 22 on the drive hub 20 are adapted to be removably placed within the primary indents 40, 50 of the blade 12 when the blade 12 is attached to the drive hub 20. In the embodiment illustrated in FIGS. 13 and 14, the primary indents 40 are configured to receive the primary drive bosses 22 and the central indent 50 is configured to receive the central drive boss 80. When the blade 12 is coupled to the corresponding drive bosses 22, 80 at the primary indents 40, 50, the driver 18 translates motion from the motor 16 to the blade 12, and moves the blade 12 in an oscillating motion to allow the plurality of teeth 28 to cut during a surgical procedure.

As best illustrated in FIG. 14, each of the primary indents 40 has inner radii 90 defined in profile between the second side 44 and the first side 42 and between the second side 44 and the third side 46. The inner radii 90 of the primary indents 40 are greater than a corresponding inner radii 94 of the drive bosses 22 when the blade 12 is coupled to the drive hub 20. Specifically, for example, the inner radii 94 between the third surface 86 and the second surface 84 of the drive bosses 22 is less than the inner radii 90 between the first side 42 and the second side 44 defining the primary indents 40. This provides clearance between corners of the drive bosses 22 and the blade 12. As such, with respect to the second surfaces 84, the drive bosses 22 only engage the attachment portion 24 in the primary indents 40 at one location (albeit along the entire thickness of the blade 12), and typically, in the center of each second surface 84, along a line passing through the rotation axis of the blade 12. Said differently, the second surfaces 84 of the drive bosses 22 contact the blade 12 in the primary indents 40 generally at the center of the second sides 44 defining the primary indents 40. By virtue of having at least one side that is curved or non-linear in profile (e.g., side 44), contact with the drive bosses 22 can be more repeatable making suitable engagement of saw blades 12 possible without requiring manufacturing at a very low tolerance.

Still referring to FIG. 14, outer radii 96 of the attachment portion 24 may be sized and shaped in profile so that the first 42 and third 46 sides contact the drive bosses 22 at more inward locations on the third 86 and first 82 surfaces of the drive bosses 22 than if the outer radii 96 were replaced by sharp edges. In this case, the larger the outer radii 96, the more inwardly contact with the drive bosses 22 occurs when coupling the blade 12 to the drive hub 20. In the embodiment shown, the drive bosses 22 have outer radii 98 at each corner between the first 82 and fourth 88 surfaces and between the fourth 88 and third surfaces 86. In each case, the outer radii 96 of the attachment portion 24 is located so that the first 42 and third 46 sides make contact with the third 86 and first 82 surfaces laterally inwardly away from the outer radii 98 of the drive bosses 22. As a result, wear on the outer corners of the drive bosses 22 is avoided. Similarly, by virtue of the additional clearance between the inner radii 90 of the blade 12 and the inner radii 94 of the drive bosses 22, wear is avoided at all corners of the drive bosses 22. In this configuration, the force, and in turn, the wear is transferred to the attachment portion 24 of the blade 12, which is a disposable part thereby resulting in less wear on the drive hub 20 allowing the drive hub 20 to have a longer life. This configuration also reduces stress on the blade 12 and makes the motion of the blade 12 less erratic.

Figure 15:
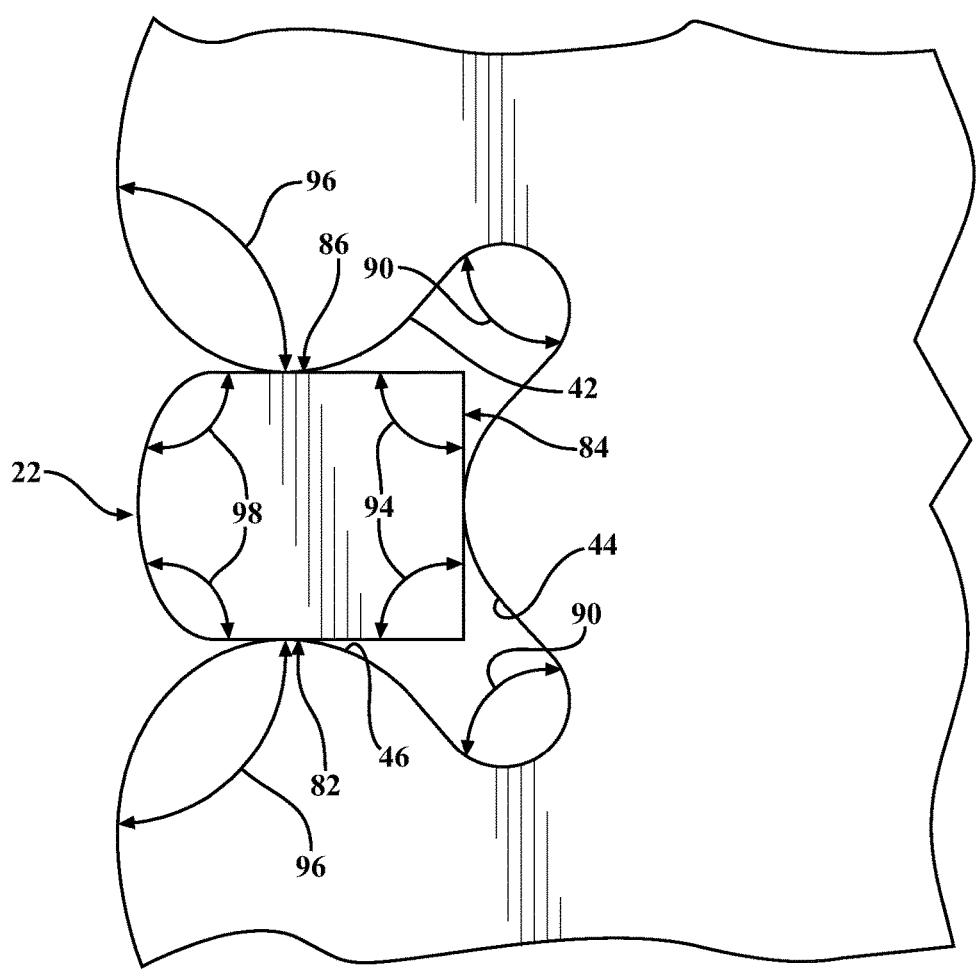
FIG. 15 is a schematic illustration of a portion of the attachment portion of the blade attached to the driver.

As illustrated in the embodiment shown in FIG. 15, a similar configuration may repeat on each of the first 42, second 44, and third 46 sides of both the indents 40. As shown in FIG. 15, each of the first 42, second 44, and third 46 sides are curved such that each of the sides 42, 44, 46 engage the drive bosses 22 at one location, as opposed to along the entire length of the surfaces 82, 84, 86 of the drive bosses 22.

FIG. 16A-E illustrates another embodiment of the blade 12. The embodiment shown in FIGS. 16A-E is intended to be exemplary in nature only and is not intended to limit the invention to a particular size or configuration.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical saw blade for being coupled to a drive hub of a surgical saw comprising:
    an attachment portion configured to be removably coupled to the drive hub and having a cutting portion opposite said attachment portion including a plurality of teeth;
    said attachment portion having a first indent and a second indent forming a first space and a second space, wherein said first indent and said second indent have at least one curved portion and said curved portion is convex such that said curved portion impinges said space,
    wherein said first indent is defined by a first side, a second side, and a third side and at least one of said first side, said second side, or said third side form said curved portion.

2. The surgical saw blade of claim 1, wherein said attachment portion of said blade has a third indent having a 'U' shape.

3. The surgical saw blade of claim 2, wherein said third indent includes a notch.

4. The surgical saw blade of claim 1, wherein said teeth are triangularly shaped.

5. The surgical saw blade of claim 4, wherein said teeth have varied thicknesses.

6. The surgical saw blade of claim 4, wherein a single tooth of said plurality of teeth has a varied thickness.

7. The surgical saw blade of claim 1, wherein said blade has a thickness of approximately 2 mm.

8. The surgical saw blade of claim 1, wherein said curved portions comprises a first curved portion and second curved portion and said first side forms said first curved portion and said third side forms said second curved portion.

9. The surgical saw blade of claim 1, wherein said second side forms said curved portion.

10. The surgical saw blade of claim 1, wherein said curved portions comprises a first curved portion, a second curved portion and a third curved portion and said first side forms said first curved portion, said second side forms said second curved portion, and said third side forms said third curved portion.

11. The surgical saw blade of claim 1, wherein said first side and said third side are convex in shape and a convex portion of said first side and said third side are facing each other.

12. The surgical saw blade of claim 1, wherein an aperture is disposed on the cutting portion.

13. The surgical saw blade of claim 12, wherein said aperture is triangular in shape.

14. The surgical saw blade of claim 1 further comprising an arrow disposed on a top surface of said blade indicating a direction of swing.

15. A surgical saw assembly coupled to a motor, said assembly comprising:
    a housing;
    a driver disposed within said housing and having a drive hub, said driver configured to be coupled to the motor;
    a blade removably coupled to said drive hub at an attachment portion and having a cutting portion opposite said attachment portion, said cutting portion including a plurality of teeth;
    said attachment portion defining a first indent and a second indent, wherein said attachment portion comprises at least one curved surface defining each of said indents-; and said drive hub including a first drive boss and a second drive boss adapted to be coupled to said blade in said first indent and said second indent, respectively; and wherein said first indent is defined by a first side, a second side, and a third side and at least one of said first side, said second side, or said third side form said curved surface, said curved surface being convexly shaped.

16. The surgical saw assembly of claim 15, wherein said first drive boss and said second drive boss have at least one linear edge.

17. The surgical saw assembly of claim 16, wherein said at least one linear edge of said first drive boss and said second drive boss engage said at least one curved portion defining said first indent and said second indent, respectively.

* * * * *